United States Patent
Li et al.

(10) Patent No.: US 10,294,219 B2
(45) Date of Patent: May 21, 2019

(54) LEDIPASVIR CRYSTAL FORM AND PREPARATION METHOD THEREOF

(71) Applicant: SHANGHAI FOREFRONT PHARMACEUTICAL CO., LTD, Shanghai (CN)

(72) Inventors: Wei Li, Shanghai (CN); Yi Ren, Shanghai (CN); Chengjun Huang, Shanghai (CN); Yanyan Zhu, Shanghai (CN); Shaojun Fu, Shanghai (CN); Gang Fu, Shanghai (CN); Zhewen Wei, Shanghai (CN)

(73) Assignee: SHANGHAI FOREFRONT PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 15/741,963

(22) PCT Filed: Jun. 24, 2016

(86) PCT No.: PCT/CN2016/087090
§ 371 (c)(1),
(2) Date: Jan. 4, 2018

(87) PCT Pub. No.: WO2017/005104
PCT Pub. Date: Jan. 12, 2017

(65) Prior Publication Data
US 2018/0194752 A1 Jul. 12, 2018

(30) Foreign Application Priority Data
Jul. 6, 2015 (CN) .......................... 2015 1 0393767

(51) Int. Cl.
*C07D 403/14* (2006.01)
*A61P 31/14* (2006.01)
*A61K 31/4439* (2006.01)

(52) U.S. Cl.
CPC ........ *C07D 403/14* (2013.01); *A61K 31/4439* (2013.01); *A61P 31/14* (2018.01); *C07B 2200/13* (2013.01)

(58) Field of Classification Search
CPC .................................................. C07D 403/14
See application file for complete search history.

(56) References Cited

U.S. PATENT DOCUMENTS

| 8,969,588 B2 * | 3/2015 | Scott .................. A61K 31/4184 |
| | | 548/300.7 |
| 9,056,860 B2 | 6/2015 | Scott et al. |
| 9,139,570 B2 * | 9/2015 | Mogalian ........... A61K 31/4184 |
| 9,682,987 B2 * | 6/2017 | Mogalian ........... A61K 31/4184 |
| 10,039,779 B2 * | 8/2018 | Chal .................... A61K 9/1623 |
| 2013/0324496 A1 * | 12/2013 | Scott .................. A61K 31/4184 |
| | | 514/52 |
| 2014/0212491 A1 * | 7/2014 | Chal .................... A61K 9/1623 |
| | | 424/474 |
| 2015/0141659 A1 | 5/2015 | Mogalian et al. |

FOREIGN PATENT DOCUMENTS

| CN | 104379584 A | 2/2015 |
| CN | 104520293 A | 4/2015 |
| CN | 104961733 A | 10/2015 |
| WO | 2014/120982 A1 | 8/2014 |

OTHER PUBLICATIONS

D Braga et al., Crystal Polymorphism and Multiple Crystal Forms, in 132 Molecular Networks: Structure Bonding, 25-50 (2009).*
Solid State Characterization of Pharmaceuticals (R.A. Storey et al., eds., 2011) (Year: 2011).*
J.O. Link et al., 57 Journal of Medicinal Chemistry, 2033-2046 (2013) (Year: 2013).*
English Translation of the International Search Report corresponding to PCT/CN2016/087090 dated Oct. 9, 2016, 2 pages.

* cited by examiner

*Primary Examiner* — Alexander R Pagano
(74) *Attorney, Agent, or Firm* — Mintz, Levin, Cohn, Ferris, Glovsky and Popeo, P.C.

(57) ABSTRACT

The present invention relates to a novel Ledipasvir (LDV) crystal form and a preparation method thereof. Specifically, disclosed is an LDV solvate. The solvate is a solvate formed by LDV and a solvent A and/or a solvent B, wherein the solvent A is acetonitrile or acetone; and the solvent B is methyl tertiary butyl ether (MTBE). Also disclosed are a preparation method and an application of the solvate. The solvate has a high purity, a good crystallization property, and better optical stability. The preparation method is simple and the process is stable. The solvate can significantly improve quality control and industrial applications of LDV-containing drugs.

17 Claims, 6 Drawing Sheets

LEDIPASVIR CRYSTAL FORM AND PREPARATION METHOD THEREOF

TECHNICAL FIELD

The present invention relates to the field of medicinal chemistry, in particular to a novel Ledipasvir crystal form and a preparation method thereof.

BACKGROUND

Ledipasvir (LDV) (The structure is shown in formula I) is a hepatitis C drug developed by Gilead, and FDA has granted a breakthrough therapy designation of LDV/SOF (Sofosbuvir) fixed dose combination that is expected to cure genotype 1 HCV patients in as short as 8 weeks without injection of interferon or combination with Ribavirin.

I

Crystal form is a term used to describe the crystalline state of a compound and encompasses polymorphs, solvates, salts, eutectics and the like. The crystal form has a profound effect on the physical and chemical properties of the compound such as stability, solubility, powder properties and the like. At the same time, the crystallization process is also an important means to remove impurities and thereby improve product quality in the pharmaceutical process.

Due to its molecular structure, Ledipasvir has poorer crystallinity and photostability. At present, Gilead's patent US20130324496A1 has claimed Ledipasvir diacetone solvate and monoacetone solvate. These two crystal forms show a better purification effect by crystallization, of which the photostability is better than that of amorphous but the degradation is still as high as 6.3% after 1.2 million lux·hours of illumination, and which can't meet the practical application demand well.

Therefore, there is an urgent need in the art to develop a new crystal form of Ledipasvir to further improve its crystallinity and stability, thereby to promote its production and application.

SUMMARY OF INVENTION

It is an object of the present invention to provide a new crystal form of Ledipasvir to further improve its crystallinity and stability thereby to promote its production and application.

In a first aspect of the present invention, there is provided a Ledipasvir solvate which is a solvate of LDV formed with component A and/or component B, wherein the component A is acetonitrile or acetone, and the component B is methyl tert-butyl ether (MTBE).

In another preferred embodiment, the solvate is a crystal.

In another preferred embodiment, the solvate is selected from the group consisting of:

(i-1) LDV-acetonitrile-MTBE ternary solvate (crystal form A);

(i-2) LDV-acetone-MTBE ternary solvate (crystal form B).

In another preferred embodiment, in the LDV-acetonitrile-MTBE ternary solvate, the molar ratio of LDV:acetonitrile:MTBE is about 1:0.9-1.5:0.7-1.2, preferably about 1:1.2-1.4:0.7-1.0, more preferably about 1:1:1 or 1:1.3:0.8.

In another preferred embodiment, in the LDV-acetone-MTBE ternary solvate, the molar ratio of LDV:acetone:MTBE is about 1:1.2-2:0.7-1.2, preferably about 1:1.5-1.8:0.9-1.1, more preferably about 1:2:1 or 1:1.7:1.

In another preferred embodiment, the LDV-acetonitrile-MTBE ternary solvate has the following X-ray powder diffraction characteristic peaks:
6.7°±0.2°, 8.8°±0.2° and 12.4°±0.2°.

In another preferred embodiment, the LDV-acetonitrile-MTBE ternary solvate has 3 or more X-ray powder diffraction characteristic peaks selected from the following group:
6.7°±0.2°, 8.8°±0.2°, 12.4°±0.2°, 18.7°±0.2°, 19.7°±0.2° and 21.5°±0.2°.

In another preferred embodiment, the LDV-acetonitrile-MTBE ternary solvate has 3 or more X-ray powder diffraction characteristic peaks selected from the following group:
6.7°±0.2°, 8.8°±0.2°, 12.4°±0.2°, 17.6°±0.2°, 18.1°±0.2°, 18.7°±0.2°, 19.7°±0.2°, 21.0°±0.2° and 21.5°±0.2°.

Figure 1:
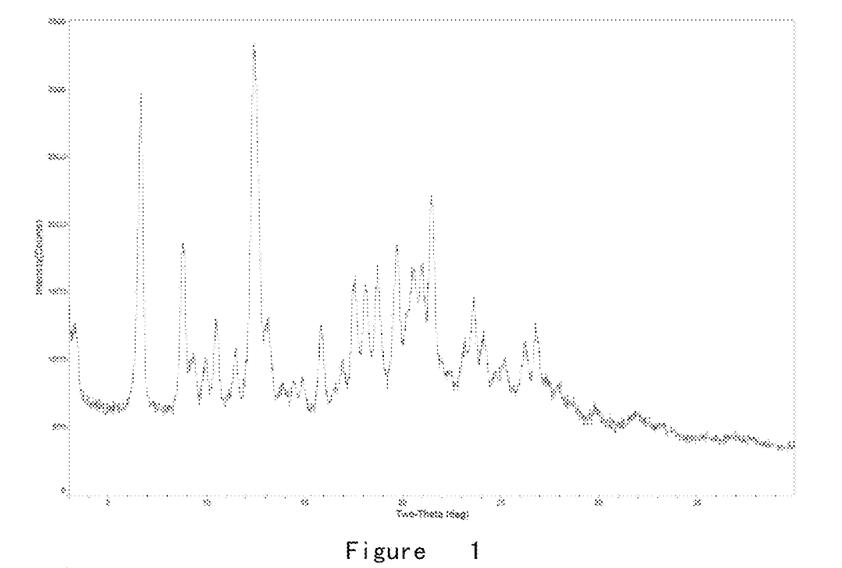
FIG. 1 is an XRD pattern of crystal form A of Example 1 of the present invention.

In another preferred embodiment, the LDV-acetonitrile-MTBE ternary solvate has an XRD pattern substantially as shown in FIG. 1.

In another preferred embodiment, the TAG pattern of the LDV-acetonitrile-MTBE ternary solvate has a weight loss of 5.5-8% at 30-120° C., preferably about 6.75%.

In another preferred embodiment, the TAG pattern of the LDV-acetonitrile-MTBE ternary solvate has a weight loss of 3.5-5.5% at 120-200° C., preferably about 4.28%.

Figure 2:
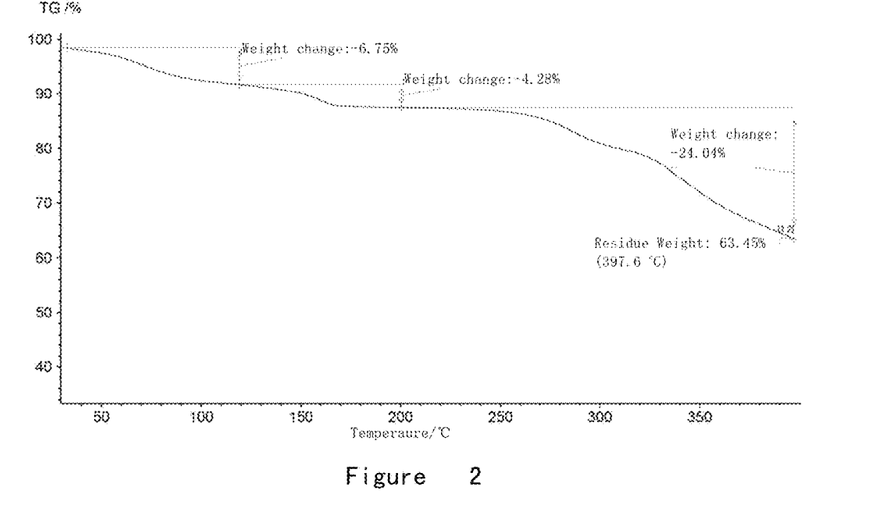
FIG. 2 is a TGA pattern of crystal form A of Example 1 of the present invention.

In another preferred embodiment, the LDV-acetonitrile-MTBE ternary solvate has a TGA pattern substantially as shown in FIG. 2.

In another preferred embodiment, the DSC pattern of the LDV-acetonitrile-MTBE ternary solvate shows a characteristic endothermic peak at 106±5° C.

In another preferred embodiment, the DSC pattern of the LDV-acetonitrile-MTBE ternary solvate shows a characteristic endothermic peak at 161±5° C.

Figure 3:
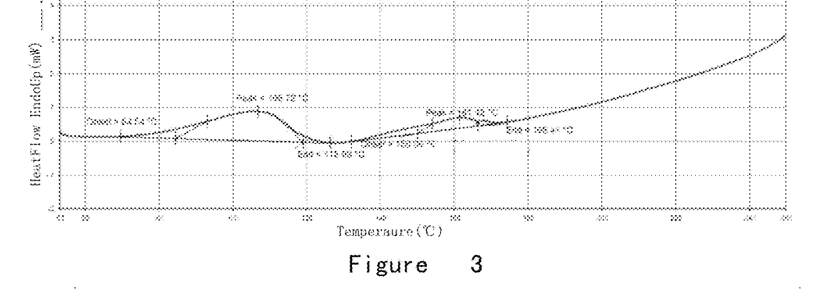
FIG. 3 is a DSC pattern of crystal form A of Example 1 of the present invention.

In another preferred embodiment, the LDV-acetonitrile-MTBE ternary solvate has a DSG pattern substantially as shown in FIG. 3.

In another preferred embodiment, the HPLC purity of the LDV-acetonitrile-MTBE ternary solvate was as high as 99.1%.

In another preferred embodiment, the LDV-acetonitrile-MTBE ternary solvate has a degradation of 2.0% after 1.2 million lux. hours of illumination.

In another preferred embodiment, the LDV-acetone-MTBE ternary solvate has the following X-ray powder diffraction characteristic peaks:

3.2°±0.2°, 6.5°±0.2° and 12.2°±0.2°.

In another preferred embodiment, the LDV-acetone-MTBE ternary solvate has 3 or more X-ray powder diffraction characteristic peaks selected from the following group:

3.2°±0.2°, 6.5°±0.2°, 8.7°±0.2°, 12.2°±0.2°, 12.4°±0.2° and 19.5°±0.2°.

In another preferred embodiment, the LDV-acetone-MTBE ternary solvate has 3 or more X-ray powder diffraction characteristic peaks selected from the following group:

3.2°±0.2°, 6.5°±0.2°, 8.7°±0.2°, 12.2°±0.2°, 12.4°±0.2°, 19.5°±0.2°, 21.2°±0.2°, 23.0°±0.2° and 23.3°±0.2°.

Figure 4:
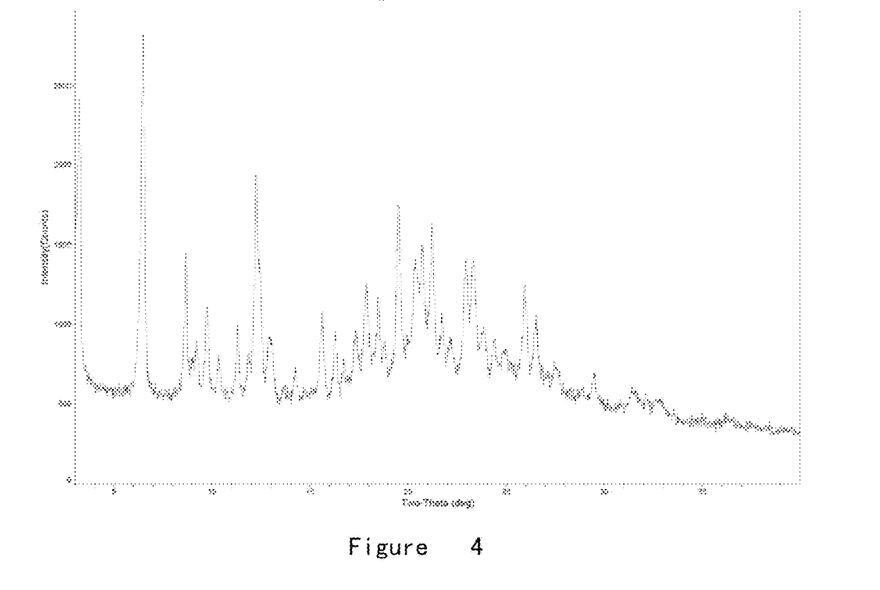
FIG. 4 is an XRD pattern of crystal form B of Example 2 of the present invention.

In another preferred embodiment, the LDV-acetone-MTBE ternary solvate has an XRD pattern substantially as shown in FIG. 4.

In another preferred embodiment, the TGA pattern of the LDV-acetone-MTBE ternary solvate has a weight loss of 9.5-11% at 30-120° C., preferably about 10.25%.

In another preferred embodiment, the TGA pattern of the LDV-acetone-MTBE ternary solvate has a weight loss of 3.5-6% at 120-200° C., preferably about 4.76%.

Figure 5:
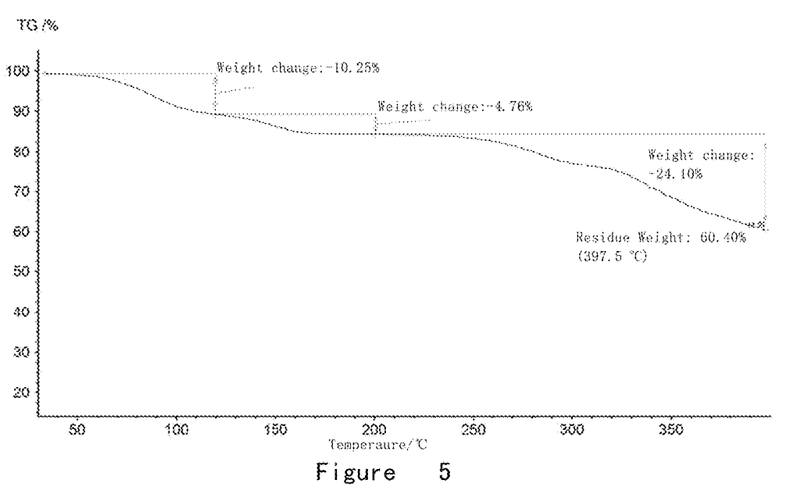
FIG. 5 is a TGA pattern of crystal form B of Example 2 of the present invention.

In another preferred embodiment, the LDV-acetone-MTBE ternary solvate has a TGA pattern substantially as shown in FIG. 5.

In another preferred embodiment, the DSC pattern of the LDV-acetone-MTBE ternary solvate shows a characteristic endothermic peak at 105±5° C.

In another preferred embodiment, the DSC pattern of the LDV-acetone-MTBE ternary solvate shows a characteristic endothermic peak at 161±5° C.

Figure 6:
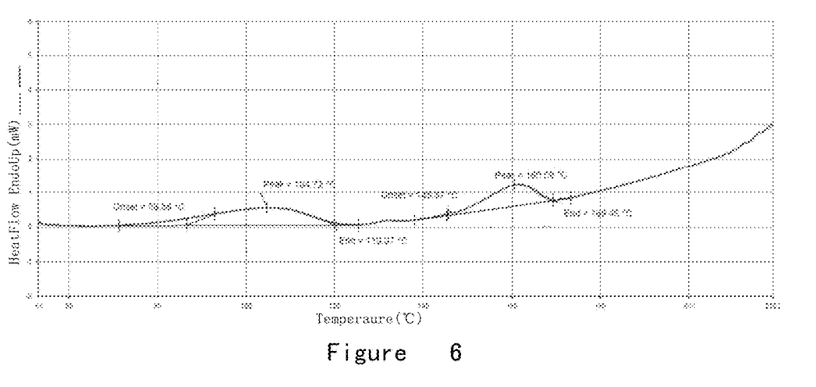
FIG. 6 is a DSC pattern of crystal form B of Example 2 of the present invention.

In another preferred embodiment, the LDV-acetone-MTBE ternary solvate has a DSG pattern substantially as shown in FIG. 6.

In another preferred embodiment, the HPLC purity of the LDV-acetone-MTBE ternary solvate was as high as 98.8%.

In another preferred embodiment, the LDV-acetone-MTBE ternary solvate has a degradation of 0.6% after 1.2 million lux. hours of illumination.

In another preferred embodiment, the solvate is selected from the group consisting of:

(ii-1) LDV-acetonitrile binary solvate (crystal form D), wherein the molar ratio of LDV:acetonitrile is 1:1.8-2.4; or (ii-2) LDV-MTB binary solvate (crystal form E), wherein the molar ratio of LDV:MTBE is 1:0.3-0.8.

In another preferred embodiment, the LDV-acetonitrile binary solvate has the following X-ray powder diffraction characteristic peaks: 6.9°±0.2°, 12.8°±0.2° and 21.6°±0.2°.

In another preferred embodiment, the LDV-acetonitrile binary solvate has 3 or more X-ray powder diffraction characteristic peaks selected from the following group:

6.9°±0.2°, 10.3°±0.2°, 12.2°±0.2°, 12.8°±0.2°, 16.3°±0.2° and 21.6°±0.2°.

Figure 8:
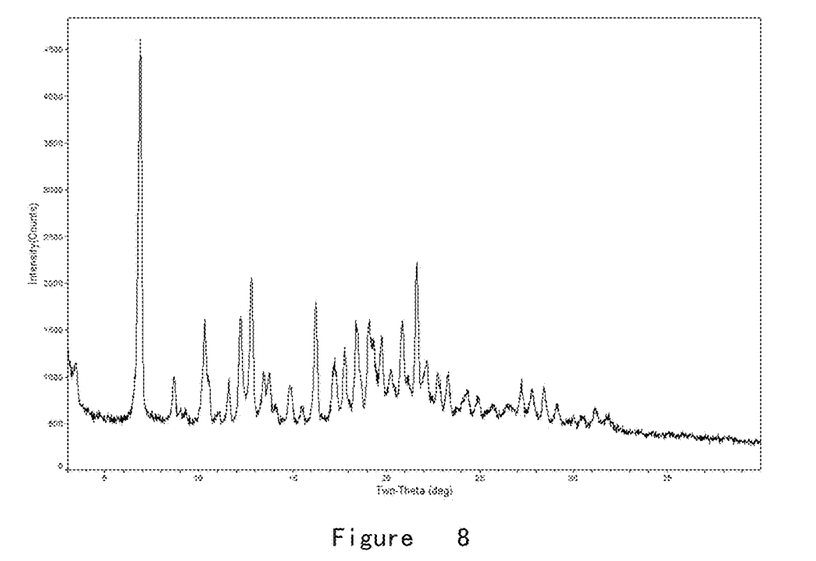
FIG. 8 is an XRD pattern of crystal form D of Example 4 of the present invention.

In another preferred embodiment, the LDV-acetonitrile binary solvate has an XRD pattern substantially as shown in FIG. 8.

In another preferred embodiment, the TGA pattern of the LDV-acetonitrile binary solvate has a weight loss of 8-10% at 40-200° C., preferably about 8.91%.

Figure 9:
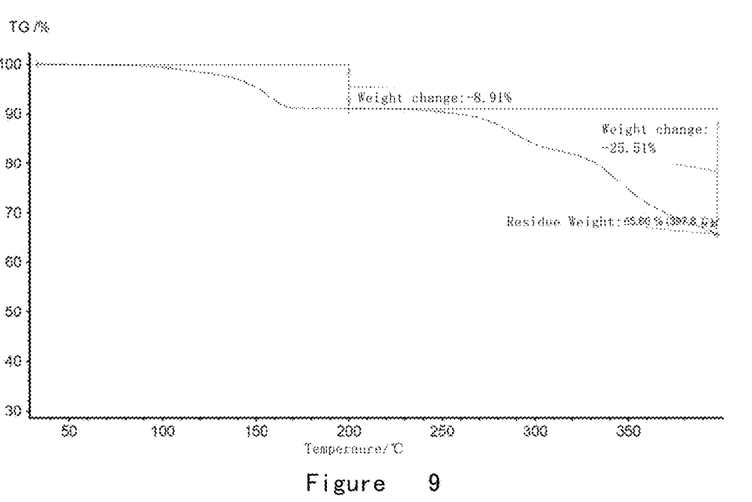
FIG. 9 is a TGA pattern of crystal form D of Example 4 of the present invention.

In another preferred embodiment, the LDV-acetonitrile binary solvate has a TGA pattern substantially as shown in FIG. 9.

In another preferred embodiment, the DSC pattern of the LDV-acetonitrile binary solvate shows a characteristic endothermic peak at 155±5° C.

Figure 10:
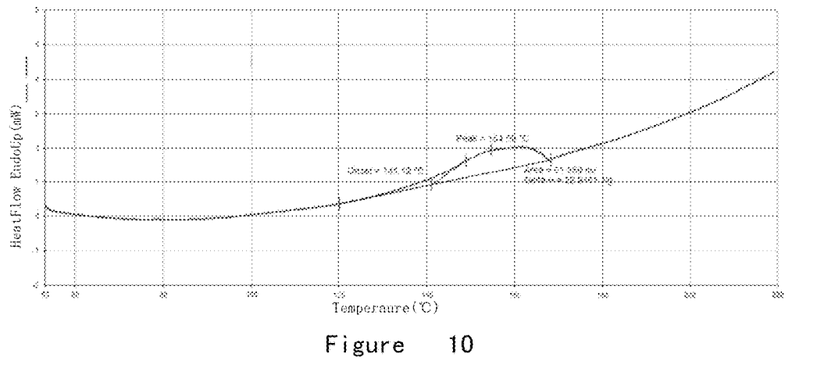
FIG. 10 is a DSC pattern of crystal form D of Example 4 of the present invention.

In another preferred embodiment, the LDV-acetonitrile binary solvate has a DSG pattern substantially as shown in FIG. 10.

In another preferred embodiment, the LDV-MTB binary solvate has the following X-ray powder diffraction characteristic peaks:

8.7°±0.2°, 12.2°±0.2° and 21.7°±0.2°.

In another preferred embodiment, the LDV-MTB binary solvate has 3 or more X-ray powder diffraction characteristic peaks selected from the following group:

7.4°±0.2°, 8.7°±0.2°, 12.2°±0.2°, 17.4°±0.2°, 19.4°±0.2° and 21.7°±0.2°.

Figure 11:
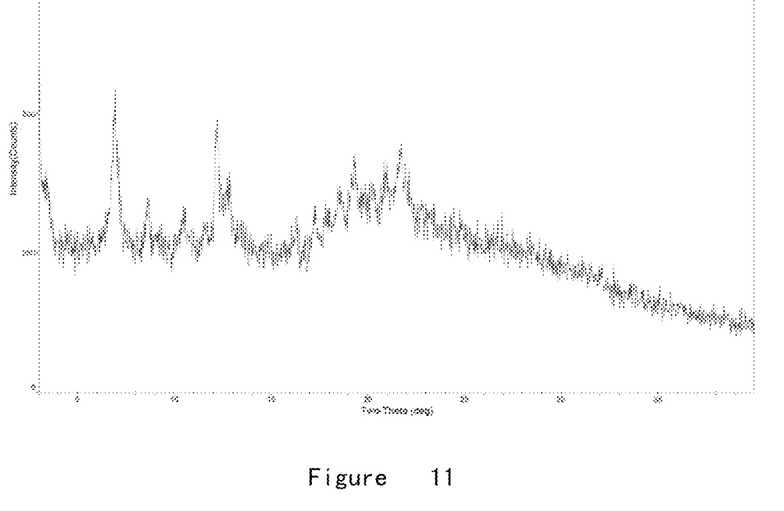
FIG. 11 is an XRD pattern of crystal form E of Example 5 of the present invention

In another preferred embodiment, the LDV-MTB binary solvate has an XRD pattern substantially as shown in FIG. 11.

In another preferred embodiment, the solvate is prepared through the method of the second aspect of the invention.

In a second aspect of the present invention, there is provided a method for preparing the solvate according to the first aspect of the present invention, comprising the steps of:

1) providing an amorphous powder of Ledipasvir, and a mixed solvent of component A and component B as described in the first aspect of the present invention;

2) mixing the amorphous powder of Ledipasvir and the mixed solvent, and crystallizing to obtain the solvate of the first aspect of the present invention.

In another preferred embodiment, the HPLC purity of the amorphous powder of Ledipasvir is 85-98%, preferably 90-98%, more preferably 95-98%.

In another preferred embodiment, the volume ratio of component A to component B in the mixed solvent is 1:1-5, preferably 1:1-4, more preferably 1:1-3.

In another preferred embodiment, the addition ratio of the amorphous powder of Ledipasvir to the mixed solvent is 10-200 mg:0.05-10 ml, preferably 20-150 mg:0.1-5 ml, more preferably 30-100 mg:0.15-2 ml.

In another preferred embodiment, the crystallization is carried out at room temperature.

In a third aspect of the present invention, there is provided a method for preparing a pharmaceutical composition comprising the steps of:

1) preparing a solid dispersion of Ledipasvir using the Ledipasvir solvate according to the first aspect of the invention as a raw material of the active ingredient Ledipasvir;

2) mixing the solid dispersion with a pharmaceutically acceptable carrier to prepare a pharmaceutical composition.

In another preferred embodiment, the Ledipasvir solvate is a crystal.

In another preferred embodiment, the Ledipasvir solvate is a crystal form A, a crystal form B or a combination thereof.

In another preferred embodiment, in step 1), the crystal of the Ledipasvir solvate is mixed with a pharmaceutically acceptable solvent (such as ethanol) and a macromolecular material, which are spray-dried and optionally cooled and/or broken, thereby producing the solid dispersion.

In another preferred embodiment, in step 1), the crystal of the Ledipasvir solvate is subjected to a melting treatment and mixed with a macromolecular material, thereby producing the solid dispersion.

In a fourth aspect of the present invention, there is provided a pharmaceutical composition, and the pharmaceutical composition comprises the solvate of the first aspect of the invention and a pharmaceutically acceptable carrier.

In another preferred embodiment, the pharmaceutical composition is prepared through the method of the third aspect of the invention.

In another preferred embodiment, the pharmaceutical composition includes a compound medicine for sofosbuvir (SOF) and Ledipasvir (LDV).

In a fifth aspect of the present invention, there is provided a use of the solvate according to the first aspect of the invention for the preparation of a medicament for the treatment of hepatitis C.

In a sixth aspect of the present invention, there is provided a method of treating or preventing hepatitis C, administering to a patient a therapeutically effective amount of the solvate of the first aspect of the present invention or the pharmaceutical composition of the fourth aspect of the present invention.

It should be understood that, within the scope of the present invention, each technical feature of the present invention described above and in the following (as examples) may be combined with each other to form a new or preferred technical solution, which is not listed here due to space limitations.

DETAILED DESCRIPTION

After a long and intensive study, the present inventors have unexpectedly prepared a Ledipasvir solvate with high purity, excellent crystallinity and better optical stability. Specifically, the present inventors have obtained a novel ternary solvate with excellent property by crystallization of amorphous powder of Ledipasvir in a mixed solvent of acetonitrile or acetone and methyl t-butyl ether. The use of the ternary solvate can greatly improve the quality control and industrial application of the drug containing Ledipasvir. On this basis, the inventors complete the present invention.

Solvate

The present invention provides a Ledipasvir solvate, which is a solvate of LDV formed with component A and/or component B, wherein the component A is acetonitrile or acetone, and the component B is methyl tert-butyl ether (MTBE).

In the present invention, the solvate is preferably a crystal.

In the present invention, the solvate is a ternary solvate of MTBE and LDV with acetonitrile or acetone.

Representatively, the ternary solvate is selected from the group consisting of:

(i-1) LDV-acetonitrile-MTBE ternary solvate (crystal form A);

(i-2) LDV-acetone-MTBE ternary solvate (crystal form B).

In the present invention, in the LDV-acetonitrile-MTBE ternary solvate and the LDV-acetone-MTBE ternary solvate, the molar ratio of each component is not particularly limited and may vary widely depending on the actual needs.

Typically, in the LDV-acetonitrile-MTBE ternary solvate, the molar ratio of LDV:acetonitrile:MTBE is about 1:0.9-1.5:0.7-1.2, preferably about 1:1.2-1.4:0.7-1.0, more preferably about 1:1:1 or 1:1.3:0.8.

Typically, in the LDV-acetone-MTBE ternary solvate, the molar ratio of LDV:acetone:MTBE is about 1:1.2-2:0.7-1.2, preferably about 1:1.5-1.8:0.9-1.1, more preferably about 1:2:1 or 1:1.7:1.

Generally, The LDV-acetonitrile-MTBE ternary solvate has the following X-ray powder diffraction characteristic peaks:

6.7°±0.2°, 8.8°±0.2° and 12.4°±0.2°.

In another preferred embodiment, the LDV-acetonitrile-MTBE ternary solvate has 3 or more X-ray powder diffraction characteristic peaks selected from the following group:

6.7°±0.2, 8.8°±0.2°, 12.4°±0.2°, 18.7°±0.2°, 19.7°±0.2° and 21.5°±0.2°.

In another preferred embodiment, the LDV-acetonitrile-MTBE ternary solvate has 3 or more X-ray powder diffraction characteristic peaks selected from the following group:

6.7°±0.2°, 8.8°±0.2°, 12.4°±0.2°, 17.6°±0.2°, 18.1°±0.2°, 18.7°±0.2°, 19.7°±0.2°, 21.0°±0.2° and 21.5°±0.2°.

In another preferred embodiment, the LDV-acetonitrile-MTBE ternary solvate has an XRD pattern substantially as shown in FIG. 1.

In another preferred embodiment, the TGA pattern of the LDV-acetonitrile-MTBE ternary solvate has a weight loss of 5.5-8% at 30-120° C., preferably about 6.75%.

In another preferred embodiment, the TGA pattern of the LDV-acetonitrile-MTBE ternary solvate has a weight loss of 3.5-5.5% at 120-200° C., preferably about 4.28%.

In another preferred embodiment, the LDV-acetonitrile-MTBE ternary solvate has a TGA pattern substantially as shown in FIG. 2.

In another preferred embodiment, the DSC pattern of the LDV-acetonitrile-MTBE ternary solvate shows a characteristic endothermic peak at 106±5° C.

In another preferred embodiment, the DSC pattern of the LDV-acetonitrile-MTBE ternary solvate shows a characteristic endothermic peak at 161±5° C.

In another preferred embodiment, the LDV-acetonitrile-MTBE ternary solvate has a DSG pattern substantially as shown in FIG. 3.

In another preferred embodiment, the HPLC purity of the LDV-acetonitrile-MTBE ternary solvate was as high as 99.1%.

In another preferred embodiment, the LDV-acetonitrile-MTBE ternary solvate has a degradation of 2.0% after 1.2 million lux. hours of illumination.

Generally, the LDV-acetone-MTBE ternary solvate has the following X-ray powder diffraction characteristic peaks:
3.2°±0.2°, 6.5°±0.2° and 12.2°±0.2°.

In another preferred embodiment, the LDV-acetone-MTBE ternary solvate has 3 or more X-ray powder diffraction characteristic peaks selected from the following group:
3.2°±0.2°, 6.5°±0.2°, 8.7°±0.2°, 12.2°±0.2°, 12.4°±0.2° and 19.5°±0.2°.

In another preferred embodiment, the LDV-acetone-MTBE ternary solvate has 3 or more X-ray powder diffraction characteristic peaks selected from the following group:
3.2°±0.2°, 6.5°±0.2°, 8.7°±0.2°, 12.2°±0.2°, 12.4°±0.2°, 19.5°±0.2°, 21.2°±0.2°, 23.0°±0.2° and 23.3°±0.2°.

In another preferred embodiment, the LDV-acetone-MTBE ternary solvate has an XRD pattern substantially as shown in FIG. 4.

In another preferred embodiment, the TGA pattern of the LDV-acetone-MTBE ternary solvate has a weight loss of 9.5-11% at 30-120° C., preferably about 10.25%.

In another preferred embodiment, the TGA pattern of the LDV-acetone-MTBE ternary solvate has a weight loss of 3.5-6% at 120-200° C., preferably about 4.76%.

In another preferred embodiment, the LDV-acetone-MTBE ternary solvate has a TGA pattern substantially as shown in FIG. 5.

In another preferred embodiment, the DSC pattern of the LDV-acetone-MTBE ternary solvate shows a characteristic endothermic peak at 105±5° C.

In another preferred embodiment, the DSC pattern of the LDV-acetone-MTBE ternary solvate shows a characteristic endothermic peak at 161±5° C.

In another preferred embodiment, the LDV-acetone-MTBE ternary solvate has a DSG pattern substantially as shown in FIG. 6.

In another preferred embodiment, the HPLC purity of the LDV-acetone-MTBE ternary solvate was as high as 98.8%.

In another preferred embodiment, the LDV-acetone-MTBE ternary solvate has a degradation of 0.6% after 1.2 million lux. hours of illumination.

In another preferred embodiment, the ternary solvate is prepared through the method of the second aspect of the invention.

In the present invention, the solvate is a binary solvate of LDV with acetonitrile or MTBE.

Typically, the binary solvate is selected from the group consisting of:
(ii-1) LDV-acetonitrile binary solvate (crystal form D), wherein the molar ratio of LDV:acetonitrile is 1:1.8-2.4; or
(ii-2) LDV-MTBE binary solvate (crystal form E), wherein the molar ratio of LDV:MTBE is 1:0.3-0.8.

In another preferred embodiment, the LDV-acetonitrile binary solvate has the following X-ray powder diffraction characteristic peaks: 6.9°±0.2°, 12.8°±0.2° and 21.6°±0.2°.

In another preferred embodiment, the LDV-acetonitrile binary solvate has 3 or more X-ray powder diffraction characteristic peaks selected from the following group:
6.9°±0.2°, 10.3°±0.2°, 12.2°±0.2°, 12.8°±0.2°, 16.3°±0.2° and 21.6°±0.2°.

In another preferred embodiment, the LDV-acetonitrile binary solvate has an XRD pattern substantially as shown in FIG. 8.

In another preferred embodiment, the TGA pattern of the LDV-acetonitrile binary solvate has a weight loss of 8-10% at 40-200° C., preferably about 8.91%.

In another preferred embodiment, the LDV-acetonitrile binary solvate has a TGA pattern substantially as shown in FIG. 9.

In another preferred embodiment, the DSC pattern of the LDV-acetonitrile binary solvate shows a characteristic endothermic peak at 155±5° C.

In another preferred embodiment, the LDV-acetonitrile binary solvate has a DSG pattern substantially as shown in FIG. 10.

In another preferred embodiment, the LDV-MTBE binary solvate has the following X-ray powder diffraction characteristic peaks:
8.7°±0.2°, 12.2°±0.2° and 21.7°±0.2°.

In another preferred embodiment, the LDV-MTBE binary solvate has 3 or more X-ray powder diffraction characteristic peaks selected from the following group:
7.4°±0.2°, 8.7°±0.2°, 12.2°±0.2°, 17.4°±0.2°, 19.4°±0.2° and 21.7°±0.2°.

In another preferred embodiment, the LDV-MTBE binary solvate has an XRD pattern substantially as shown in FIG. 11.

Preparation Method of the Solvate

The invention further provides a method for preparing the solvate, comprising the following steps of:
1) providing an amorphous powder of Ledipasvir, and a mixed solvent of component A and component B;
2) mixing the amorphous powder of Ledipasvir and the mixed solvent, and crystallizing to obtain the solvate.

In another preferred embodiment, the HPLC purity of the amorphous powder of Ledipasvir is 85-98%, preferably 90-98%, more preferably 95-98%.

In the present invention, the volume ratio of component A to component B in the mixed solvent is not particularly limited and may vary widely depending on the actual needs.

Typically, the volume ratio of component A to component B in the mixed solvent is 1:1-5, preferably 1:1-4, more preferably 1:1-3.

In the present invention, the addition ratio of the amorphous powder of Ledipasvir to the mixed solvent is not particularly limited and may vary widely depending on the actual needs.

Typically, the addition ratio of the amorphous powder of Ledipasvir to the mixed solvent is 10-200 mg:0.05-10 ml, preferably 20-150 mg:0.1-5 ml, more preferably 30-100 mg:0.15-2 ml.

In another preferred embodiment, the crystallization is carried out at room temperature.

In the present invention, the crystallization temperature, time, pressure, aeration and stirring conditions are not particularly limited, and those skilled in the art can select appropriate conditions according to actual needs.

Typically, the crystal form C of Ledipasvir is prepared as follows:

The present invention provides a preparation method of the crystal form C of Ledipasvir, comprising the step of:
(i-1) preparing the crystal form C of Ledipasvir by placing the crystal form A of Ledipasvir under conditions of a certain pressure, temperature, ventilation and the like to desolvate the crystal form A of Ledipasvir partially.

In the step (i-1), the pressure, temperature, time, ventilation and the like are not particularly limited, and those skilled in the art can select suitable conditions according to actual needs.

Typically, the crystal form D of Ledipasvir is prepared as follows:

The present invention provides a preparation method of the crystal form D of Ledipasvir, which comprises the step of:

(i-2) either the crystal form A or the crystal form B of Ledipasvir powder is added into ACN to prepare a suspension, which is left for a suitable time to complete the crystal transformation.

In the step (i-2), the temperature, time, stirring and the like are not particularly limited, and those skilled in the art can select suitable conditions according to actual needs.

Typically, the crystal Form E of Ledipasvir is prepared as follows:

The present invention provides a method for preparing the crystal Form E of Ledipasvir, comprising the step of:

(i-3) preparing the crystal form E of Ledipasvir by placing the crystal form B of Ledipasvir under conditions of a certain pressure, temperature and ventilation to desolvate the crystal form B of Ledipasvir partially.

In the step (i-3), the pressure, temperature, time, ventilation and the like are not particularly limited, and those skilled in the art can select suitable conditions according to actual needs.

Pharmaceutical Composition and its Preparation Method

The invention further provides a method for preparing a pharmaceutical composition, comprising the steps of:

1) preparing a solid dispersion of Ledipasvir using the Ledipasvir solvate as a raw material of the active ingredient Ledipasvir;

2) mixing the solid dispersion with a pharmaceutically acceptable carrier to prepare a pharmaceutical composition.

In another preferred embodiment, the Ledipasvir solvate is a crystal.

In another preferred embodiment, the Ledipasvir solvate is a crystal form A, a crystal form B or a combination thereof.

In another preferred embodiment, in step 1), the crystal of the Ledipasvir solvate is mixed with a pharmaceutically acceptable solvent (such as ethanol) and a macromolecular material, which are spray-dried and optionally cooled and/or broken, thereby producing the solid dispersion.

In another preferred embodiment, in step 1), the crystal of the Ledipasvir solvate is subjected to a melting treatment and mixed with a macromolecular material, thereby producing the solid dispersion.

The invention further provides a pharmaceutical composition, and the pharmaceutical composition comprises the solvate and a pharmaceutically acceptable carrier.

In another preferred embodiment, the pharmaceutical composition is prepared through the method of the third aspect of the invention.

Representatively, the pharmaceutical composition includes (but not limited to) a compound medicine for sofosbuvir (SOF) and Ledipasvir (LDV).

The amount of the solvate of the present invention or the pharmaceutical composition thereof to be administered varies depending on the patient's age, gender, race, condition and the like.

The compounds of the present invention may be administered together with or in combination with other drugs or active ingredients.

In the present invention, the administration mode of the solvate or pharmaceutical composition is not particularly limited. Administration modes that are the same or similar to those of conventional Ledipasvir may be used, including but not limited to: oral, transdermal, intravenous, intramuscular, topical administration, and the like.

Application

The invention further provides a use of the solvate or the pharmaceutical composition, for the preparation of a medicament for the treatment of hepatitis C.

The invention further provides a method for treating or preventing hepatitis C, administering to the patient a therapeutically effective amount of said solvate or said pharmaceutical composition.

Compared with the prior art, the present invention has the following main advantages:

(1) the solvate has excellent crystallinity and impurity removal effects, which is favorable for preparing high-quality Ledipasvir APIs;

(2) the solvate has excellent optical stability, which is conducive to stable quality control and industrial application;

(3) the preparation method of the solvate is simple in operation, easy to control, good in reproducibility, stable in process and suitable for industrialization;

(4) the solvate has excellent powder characteristics and is suitable for the subsequent production of pharmaceutical preparations.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions or the manufacturer's proposed conditions. Unless otherwise indicated, percentages and parts are by weight.

Unless otherwise defined, all professional and scientific terms used herein have the same meanings as commonly understood by the skilled in the art. In addition, any methods and materials similar or equivalent to those described may be used in the methods of the present invention. The preferred methods and materials described herein are for illustrative purposes only.

General Test Methods

In the present invention, the crystal was subjected to the following series of general tests.

X-ray Diffraction (XRD) is a structural analysis method that uses the X-ray diffraction of crystal to analyze the internal distribution of atoms in the space. When a certain wavelength of X-ray is irradiated on a crystalline substance, the X-rays scatter due to the regular arrangement of atoms or ions in the crystal, and the scattered X-rays are phase intensified in some directions so as to display a unique diffraction phenomenon corresponding to the crystallize Structure.

In the present invention, The test parameters of XRD are as follows: Instrument Model: Bruker D8 Advance X-ray powder diffractometer; Target: Cu-K$_\alpha$ (tube voltage 40 KV, tube current 40 mA); Scanning range: 3-40° (2-Theta); Step: 0.02°; Scanning rate: 1 step/second.

Differential Scanning Calorimeter (DSC) is a technique for determining the heat difference between the sample and an inert reference (commonly used $\alpha$-Al$_2$O$_3$) as a function of temperature through program-controlled heating or cooling. DSC test is suitable for the analysis of sample under a melting decomposition state, a mixed crystal state, a crystal transformation state and so on.

In the present invention, the test parameters for the DSC are as follows: Instrument Model: Perkin Elmer DSC 8500;

Crucible: Aluminum crucible; Scanned from 50° C. to 220° C. at a ramp rate of 10° C./min under nitrogen purge.

Thermo Gravimetric Analysis (TGA) is an analytical technique for determining the mass of a substance as a function of temperature under program-controlled temperature conditions. Thermo gravimetric analysis can obtain the heat generated by the thermal change of the sample and is suitable for checking the loss of crystal solvent or crystal water in a crystal molecule or the process and the value of a sample sublimation and decomposition, and can effectively distinguishing whether the substance contains crystal solvent or crystal water composition.

In the present invention, the test parameters of the TGA are as follows: Instrument Model: Netzsch TG 209F3; Crucible: Alumina crucible; Temperature range: 30-400° C.; Scanning rate: 10° C./min; Purge: 25 mL/min; Protection gas: 15 mL/min.

High Performance Liquid Chromatography (HPLC) uses a liquid as the mobile phase and a high-pressure liquid infusion system and pumps a mobile phase such as single solvents with different polarities or a mixed solvent with different ratios, or a buffer into a chromatographic column equipped with a stationary phase and then the ingredients are separated and flew into the detector for testing, so as to achieve the analysis of the sample.

In the present invention, the experimental parameters of HPLC are as follows: Instrument Model: Agilent1260; Column: Xbridge C18, 4.6×150 mm; Mobile Phase: Acetonitrile and Water; Detection Wavelength: 220 nm.

Gas chromatography uses an inert gas as the mobile phase and the different distribution coefficient of each component in the sample between the gas phase and the stationary phase in the column. The components are repeatedly distributed several times between the two phases when the vaporized sample is run after it is carried by the gas into the column, and after running through a certain length in the column, they are separated from each other and sequentially leave the column to enter the detector, thereby realizing the analysis of the sample.

In the present invention, the test parameters of the GC are as follows: Instrument Model: SHIMADZU GC2014; Column: DB624, 0.25 mm, 30 m; Mobile Phase: $N_2$; Detector: FID.

EXAMPLE 1

Preparation of Crystal Form A of Ledipasvir 100 mg of Ledipasvir amorphous powder was weighed into a 1.5 ml centrifuge tube and 0.25 ml of mixed solvent of acetonitrile (ACN) and methyl tert-butyl ether (MTBE) (volume ratio 1:3) was added, dissolved under ultrasound. The solution was placed under airtight condition at room temperature. Solid precipitates were observed after 3 days and confirmed as crystals by a polarizing microscope.

The centrifuge tube was centrifuged in an Eppendorf minispin for 5 minutes at 12000 rpm. The supernatant was removed and the isolated solid was dried at room temperature for 1 hour to give the crystal form A (LDV-acetonitrile-MTBE ternary solvate).

Results

The product obtained in Example 1 was examined by XRD, DSC and TGA.

FIG. 1 is an XRD pattern of crystal form A of Example 1 of the present invention. It can be seen from FIG. 1 that the main diffraction peaks and the relative intensities of crystal form A are shown in Table 1.

TABLE 1

XRD data of crystal form A of Ledipasvir

| 2θ position[°] | Relative intensities [%] |
|---|---|
| 6.7 | 90.0 |
| 8.8 | 45.6 |
| 9.3 | 12.9 |
| 10.5 | 23.3 |
| 12.4 | 100.0 |
| 15.8 | 22.8 |
| 17.6 | 26.7 |
| 18.1 | 26.4 |
| 18.7 | 27.8 |
| 19.7 | 32.2 |
| 20.5 | 18.8 |
| 21.0 | 25.8 |
| 21.5 | 38.7 |
| 23.2 | 10.6 |
| 23.7 | 24.9 |
| 24.1 | 11.9 |
| 26.8 | 19.6 |

FIG. 2 is a TGA pattern of crystal form A of Example 1 of the present invention.

It can be seen from FIG. 2 that the thermogravimetric curve of crystal form A has two distinct weightless steps between 30-200° C.: 6.75% of weight loss at 30-120° C. and 4.28% of weight loss at 120-200° C.

FIG. 3 is a DSC pattern of crystal form A of Example 1 of the present invention. It can see from FIG. 3 that the heat flow curve of crystal form A has two endothermic peaks between 50-220° C.: the peak temperatures are 106° C. and 161° C. respectively.

The results of HPLC analysis show that the HPLC purity can be drastically improved to 98.6% after the crude Ledipasvir with an HPLC purity of 85.7% is crystallized to crystal form A by the method described in Example 1. Further, the HPLC purity of crystal form A obtained can also be further improved to 99.1% after the Ledipasvir amorphous powder with an HPLC purity of 98.4% is crystallized to crystal form A by the method described in Example 1. This shows that the impurities in Ledipasvir can be removed effectively and the purity of the product can be improved significantly after the crude Ledipasvir is crystallized to crystal form A by the crystallization method described in Example 1.

The results of GC analysis show that the Ledipasvir crystal form A obtained in Example 1 contains 5.3 wt % of ACN and 6.9 wt % of MTBE. According to the results of TGA and DSC, crystal form A should be a cosolvate of Ledipasvir, that is crystal form A is a ternary solvate composed of Ledipasvir, ACN and MTBE.

EXAMPLE 2

Preparation of Crystal Form B of Ledipasvir 40 mg of Ledipasvir amorphous powder was weighed into a 1.5 ml centrifuge tube, and 0.2 ml of mixed solvent of acetone and MTBE (volume ratio of 1:2) was added to form a suspension. The suspension was shaken for 3 days at room temperature. Solid precipitates were observed after 3 days and confirmed as crystals by a polarizing microscope.

The centrifuge tube was centrifuged in a centrifuge for 5 minutes at 12000 rpm, The supernatant was removed and the isolated solid was dried at room temperature for 1 hour to give the crystal form B (LDV-acetone-MTBE ternary solvate).

Results

FIG. 4 is an XRD pattern of crystal form B of Example 2 of the present invention. It can be seen from FIG. 4 that the main diffraction peaks and the relative intensities of crystal form B obtained in Example 2 are shown in Table 2.

TABLE 2

XRD data of crystal form B of Ledipasvir

| 2θ position[°] | Relative intensities [%] |
| --- | --- |
| 3.2 | 80.6 |
| 6.5 | 100.0 |
| 8.7 | 39.2 |
| 9.2 | 14.1 |
| 9.8 | 23.2 |
| 11.3 | 19.6 |
| 12.2 | 60.1 |
| 12.4 | 35.8 |
| 12.9 | 13.6 |
| 15.6 | 23.0 |
| 16.3 | 15.7 |
| 17.3 | 11.1 |
| 17.9 | 22.5 |
| 18.5 | 20.1 |
| 19.5 | 42.4 |
| 20.4 | 21.1 |
| 20.7 | 28.7 |
| 21.2 | 30.2 |
| 21.7 | 12.0 |
| 23.0 | 29.1 |
| 23.3 | 31.2 |
| 25.9 | 24.8 |
| 26.6 | 17.8 |

FIG. 5 is a TGA pattern of crystal form B of Example 2 of the present invention.

It can be seen from FIG. 5 that the thermogravimetric curve of crystal form B has two distinct weightless steps between 30-200° C.: 10.25% of weight loss at 30-120° C. and 4.76% of weight loss at 120-200° C.

FIG. 6 is a DSC pattern of crystal form B of Example 2 of the present invention. It can be seen from FIG. 6 that the heat flow curve of crystal form B has two endothermic peaks between 50-220° C.: the peak temperatures are 105° C. and 161° C. respectively.

The results of HPLC analysis show that the HPLC purity can be drastically improved to 97.6% after the crude Ledipasvir with an HPLC purity of 85.7% is crystallized to crystal form B by the method described in Example 2. Further, the HPLC purity of crystal form B obtained can also be further improved to 98.8% after the Ledipasvir amorphous powder with an HPLC purity of 98.4% is crystallized to crystal form B by the method described in Example 2. This shows that the impurities in Ledipasvir can be removed effectively and the purity of the product can be improved significantly after the crude Ledipasvir is crystallized to crystal form B by the crystallization method described in Example 2.

The results of GC analysis show that the Ledipasvir crystal form B obtained in Example 2 contains 9.0 wt % of acetone and 7.9 wt % of MTBE. According to the testing results of TGA and DSC, crystal form B should be a cosolvate of Ledipasvir with acetone and MTBE, that is crystal form B is a ternary solvate composed of Ledipasvir, acetone and MTBE.

EXAMPLE 3

Preparation of Crystal Form C of Ledipasvir 10 mg of Ledipasvir crystal form A was weighed to TGA sample plate, and placed on a NETZSCH TG 209F3 thermogravimetric analyzer, heated to 120° C. at a heating rate of 10° C./min and then rapidly cooled to room temperature under protective nitrogen to obtain crystal form C.

Results

Figure 7:
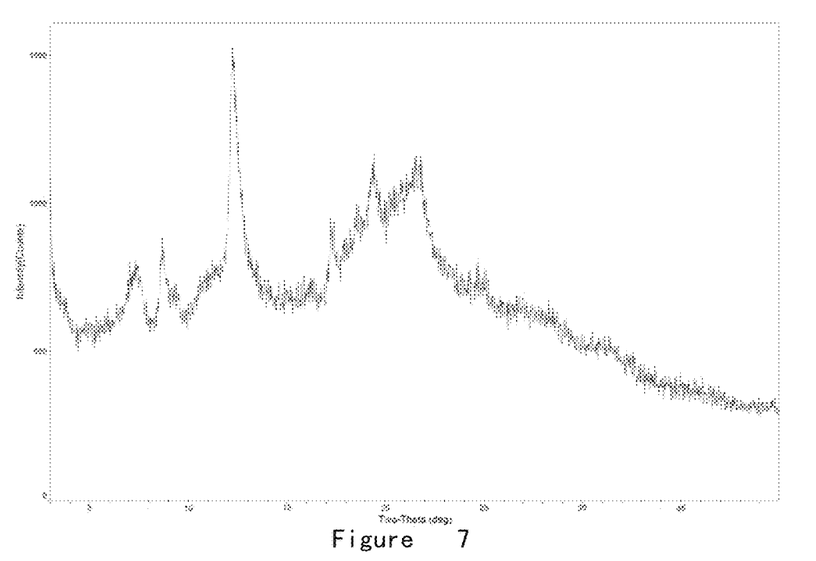
FIG. 7 is an XRD pattern of crystal form C of Example 3 of the present invention.

FIG. 7 is an XRD pattern of crystal form C of Example 3 of the present invention. It can be seen from FIG. 7 that the main diffraction peaks and the relative intensities of crystal form C are shown in Table 3.

TABLE 3

XRD data of crystal form C of Ledipasvir

| 2θ position[°] | Relative intensities [%] |
| --- | --- |
| 7.4 | 23.5 |
| 8.7 | 33.5 |
| 9.3 | 12.7 |
| 12.2 | 100.0 |
| 17.4 | 20.9 |
| 19.4 | 25.1 |
| 21.7 | 26.9 |

The results of GC analysis show that the Ledipasvir crystal form C obtained in Example 3 contains 2.1 wt % of MTBE. Thus, crystal form C is the partially desolvated product of crystal form A.

EXAMPLE 4

Preparation of Crystal Form D of Ledipasvir 100 mg of Ledipasvir crystal form B was weighed into a 1.5 ml centrifuge tube, and 200 μL of ACN was added to form a suspension. The suspension was shaken for 3 days at room temperature. Solid precipitates were observed after 3 days and confirmed as crystals by a polarizing microscope.

The centrifuge tube was centrifuged in a centrifuge for 5 minutes at 12000 rpm, The supernatant was removed and the isolated solid was dried at room temperature under nitrogen for 1 hour to give the crystal form D (LDV-acetonitrile binary solvate).

Results

FIG. 8 is an XRD pattern of crystal form D of Example 4 of the present invention. It can be seen from FIG. 8 that the main diffraction peaks and the relative intensities of crystal form D obtained in Example 4 are shown in Table 4.

TABLE 4

XRD data of crystal form D of Ledipasvir

| 2θ position[°] | Relative intensities [%] |
| --- | --- |
| 6.9 | 100.0 |
| 8.7 | 11.7 |
| 10.3 | 26.6 |
| 11.6 | 11.0 |
| 12.2 | 26.3 |
| 12.8 | 35.9 |
| 13.5 | 11.4 |
| 13.8 | 11.7 |
| 16.3 | 30.8 |
| 17.3 | 14.7 |
| 17.8 | 16.2 |
| 18.4 | 22.2 |
| 19.1 | 20.9 |
| 19.3 | 16.0 |
| 19.7 | 16.5 |
| 20.9 | 19.5 |

TABLE 4-continued

XRD data of crystal form D of Ledipasvir

| 2θ position[°] | Relative intensities [%] |
|---|---|
| 21.6 | 34.8 |
| 22.2 | 10.3 |

FIG. 9 is a TGA pattern of crystal form D of Example 4 of the present invention. It can be seen from FIG. 9 that the thermogravimetric curve of crystal form D has a distinct 8.91 wt % of weightless steps between 40-200° C.

FIG. 10 is a DSC pattern of crystal form D of Example 4 of the present invention.

It can see from FIG. 10 that the heat flow curve of crystal form D has a endothermic peak between 50-220° C.: the peak temperature is 154.5° C.

According to the molecular weight of Ledipasvir and acetonitrile and the DSC and TGA detection results, the crystal form D of Ledipasvir should be a bis-acetonitrile solvate of Ledipasvir.

EXAMPLE 5

Preparation of Crystal Form E of Ledipasvir 10 mg of Ledipasvir crystal form B was weighed to TGA sample plate, and placed on a NETZSCH TG 209F3 thermogravimetric analyzer, heated to 120° C. at a heating rate of 10° C./min and then rapidly cooled to room temperature under protective nitrogen to obtain crystal form E (LDV-MTB binary solvate).

Results

FIG. 11 is an XRD pattern of crystal form E of Example 5 of the present invention. It can be seen from FIG. 11 that the main diffraction peaks and the relative intensities of crystal form E obtained in Example 5 are shown in Table 5.

TABLE 5

XRPD data of crystal form E of Ledipasvir

| 2θ position[°] | Relative intensities [%] |
|---|---|
| 7.4 | 23.5 |
| 8.7 | 33.5 |
| 9.3 | 12.7 |
| 12.2 | 100.0 |
| 17.4 | 20.9 |
| 19.4 | 25.1 |
| 21.7 | 26.9 |

The results of GC analysis show that the crystal form E of Ledipasvir contains 4.5 wt % of MTBE. Thus, crystal form E is the partially desolvated product of crystal form B. According to the molecular weights of MTBE and Ledipasvir, crystal form E should be a semi-MTBE solvate of Ledipasvir.

EXAMPLE 6

Light Stability Assessment (1) The light stability of crystal form A and crystal form B of Ledipasvir were studied. Samples of different crystal forms were placed in a watch glass and spread to a thin layer with thickness of no more than 1 mm, placed in a LS-3000 light test chamber with a light intensity of 4400 lux for 12 days.

(2) The purity of the sample after illumination was checked by HPLC and compared with the initial purity. The results showed that the HPLC purity of Ledipasvir crystal form A decreased by 2.0% and the HPLC purity of Ledipasvir crystal form B decreased by 0.6% after 1.2 million lux·hours of illumination.

(3) the light stability of Ledipasvir crystal form A and crystal form B is better compared with the light stability data of the crystal form reported in US20130324496A1 (Table 6).

TABLE 6

Light Stability of Different Crystal Form of Ledipasvir

| Crystal Form | Light conditions | HPLC purity decreased, % |
|---|---|---|
| crystal form A of Ledipasvir | 1.2 million lux · hours | 2.0 |
| crystal form B of Ledipasvir |  | 0.6 |
| *Ledipasvir amorphous |  | 8.3 |
| *crystal form II of Ledipasvir |  | 6.3 |
| *D-tartrate of Ledipasvir |  | 2.6 |
| *crystal form I of Ledipasvir | 900,000 lux · hours | 6.6 |

*Data is from US20130324496A1

EXAMPLE 7

Polymorphism Studies Based on Crystal Form A and Crystal Form B (1) Based on the double-step thermogravimetric curves of crystal form A and crystal form B, the changes of two crystal forms at different temperatures were studied. The results are shown in Table 7.

TABLE 7

Changes of crystal form of crystal form A and crystal form B of Ledipasvir at different temperatures

| crystal form A of Ledipasvir | Crystal Form |
|---|---|
| Room temperature | crystal form A |
| 120° C., nitrogen protection | crystal form C |
| 180° C., nitrogen protection | amorphous form |

| crystal form B of Ledipasvir | crystal form |
|---|---|
| Room temperature | crystal form B |
| 120° C., nitrogen protection | crystal form E |
| 180° C., nitrogen protection | amorphous form |

(2) Solvent-based screening: 100 mg of crystal form A or 100 mg of crystal form B is suspended in 200 μL of different solvents and the changes of crystal form are monitored. The results are shown in Table 8.

TABLE 8

Solvent-based screening results

| Solvent | crystal form A of Ledipasvir | crystal form B of Ledipasvir |
|---|---|---|
| Acetone | * mixture of monoacetone and diacetone solvate | * mixture of monoacetone and diacetone solvate |
| MTBE | amorphous form | amorphous form |
| ACN | crystal form D | crystal form D |
| Ethyl acetate | solution | solution |

* See US20130324496A1

Figure 12:
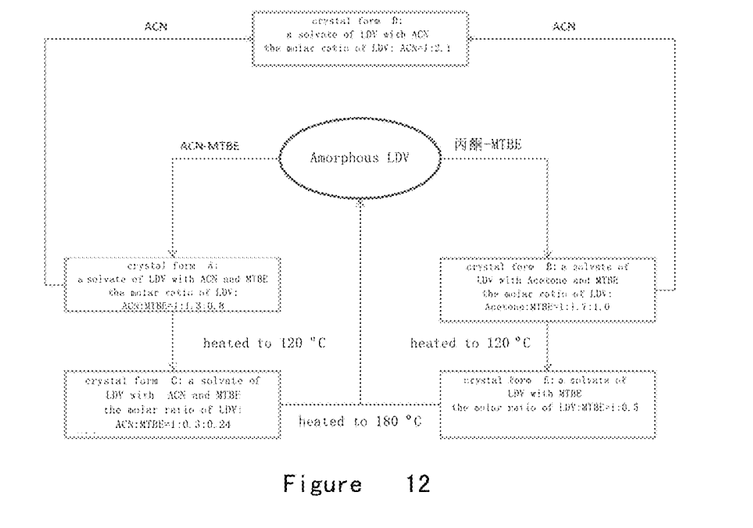
FIG. 12 is a graph showing the relationship among each crystal form of the present invention.

FIG. 12 is a graph showing the relationship among each crystal form of the present invention. It can be seen from the above polymorphism studies and FIG. 12 that the amorphous of Ledipasvir is crystallized in the ACN-MTBE solvent system to form crystal form A which is a solvate of ACN and MTBE, a part of ACN and MTBE were removed from crystal form A at 120° C. to form crystal form C which is further heated to remove the solvent completely to form amorphous. The amorphous of Ledipasvir is crystallized in the acetone-MTBE solvent system to form crystal form B which is a solvate of acetone and MTBE, acetone and a part of MTBE were removed from crystal form B at 120° C. to form crystal form E which is a semi-MTBE solvate of Ledipasvir, the crystal form E is further heated to remove the solvent completely to form amorphous. Crystal form A and crystal form B were suspended in ACN to convert to crystal form D which is a bis-acetonitrile solvate of Ledipasvir.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

What is claimed is:

1. A Ledipasvir solvate, wherein which is a solvate of LDV formed with component A and component B, wherein the component A is acetonitrile or acetone, and the component B is methyl tert-butyl ether (MTBE); and the solvate is selected from the group consisting of:
   (i-1) LDV-acetonitrile-MTBE ternary solvate (crystal form A); and
   (i-2) LDV-acetone-MTBE ternary solvate (crystal form B).

2. The solvate of claim 1, wherein The LDV-acetonitrile-MTBE ternary solvate has the following X-ray powder diffraction characteristic peaks:

6.7°±0.2°, 8.8°±0.2° and 12.4°±0.2°.

3. The solvate of claim 1, wherein the LDV-acetone-MTBE ternary solvate has the following X-ray powder diffraction characteristic peaks:

3.2°±0.2°, 6.5°±0.2° and 12.2°±0.2°.

4. A method for preparing the solvate of claim 1, the method comprising the steps of:
   1) providing an amorphous powder of Ledipasvir, and a mixed solvent of component A and component B; and
   2) mixing the amorphous powder of Ledipasvir and the mixed solvent, and crystallizing to obtain the solvate of claim 1,
   wherein the component A is acetonitrile or acetone, and the component B is methyl tert-butyl ether (MTBE).

5. A method for preparing a pharmaceutical composition, the method comprising the steps of:
   1) preparing a solid dispersion of Ledipasvir using the Ledipasvir solvate of claim 1 as a raw material of the active ingredient Ledipasvir;
   2) mixing the solid dispersion with a pharmaceutically acceptable carrier to prepare the pharmaceutical composition.

6. A pharmaceutical composition, wherein the pharmaceutical composition comprises the solvate of claim 1 and a pharmaceutically acceptable carrier.

7. A method for treating hepatitis C comprising administering to a subject in need thereof an effective amount of the solvate of claim 1 or the pharmaceutical composition of claim 6.

8. The solvate of claim 1, wherein in the LDV-acetonitrile-MTBE ternary solvate, the molar ratio of LDV: acetonitrile: MTBE is about 1:0.9-1.5:0.7-1.2.

9. The solvate of claim 1, wherein in the LDV-acetone-MTBE ternary solvate, the molar ratio of LDV: acetone: MTBE is about 1:1.2-2:0.7-1.2.

10. The solvate of claim 1, wherein the TAG pattern of the LDV-acetonitrile-MTBE ternary solvate has a weight loss of 5.5-8% at 30-120° C.

11. The solvate of claim 1, wherein the TAG pattern of the LDV-acetonitrile-MTBE ternary solvate has a weight loss of 3.5-5.5% at 120-200° C.

12. The solvate of claim 1, wherein the DSC pattern of the LDV-acetonitrile-MTBE ternary solvate has a characteristic endothermic peak at 106±5° C.

13. The solvate of claim 1, wherein the DSC pattern of the LDV-acetonitrile-MTBE ternary solvate has a characteristic endothermic peak at 161±5° C.

14. The solvate of claim 1, wherein the TGA pattern of the LDV-acetone-MTBE ternary solvate has a weight loss of 9.5-11% at 30-120° C.

15. The solvate of claim 1, wherein the TGA pattern of the LDV-acetone-MTBE ternary solvate has a weight loss of 3.5-6% at 120-200° C.

16. The solvate of claim 1, wherein the DSC pattern of the LDV-acetone-MTBE ternary solvate has a characteristic endothermic peak at 105±5° C.

17. The solvate of claim 1, wherein the DSC pattern of the LDV-acetone-MTBE ternary solvate has a characteristic endothermic peak at 161±5° C.

* * * * *